United States Patent [19]

Quimby et al.

[11] Patent Number: 5,151,371
[45] Date of Patent: Sep. 29, 1992

[54] METHOD AND SCAVENGER GAS FOR THE ANALYSIS OF OXYGEN-CONTAINING COMPONENTS USING ATOMIC EMISSION SPECTROMETRY

[75] Inventors: Bruce D. Quimby, Landenberg, Pa.; James J. Sullivan, Newark, Del.

[73] Assignee: Hewlett-Packard Company, Palo Alto, Calif.

[21] Appl. No.: 394,316

[22] Filed: Aug. 14, 1989

Related U.S. Application Data

[63] Continuation of Ser. No. 64,041, Jun. 18, 1987, abandoned.

[51] Int. Cl.$^5$ .............................. G01N 21/73
[52] U.S. Cl. ................... 436/127; 136/161; 136/166; 136/171; 356/316
[58] Field of Search ............. 436/127, 133, 134, 136, 436/161, 166, 171; 356/316

[56] References Cited

U.S. PATENT DOCUMENTS

| | | | |
|---|---|---|---|
| 3,837,808 | 9/1974 | Sugimoto et al. | 436/136 |
| 3,887,280 | 6/1975 | McLean et al. | 356/85 |
| 3,945,799 | 3/1976 | Honma | 436/127 |
| 4,234,315 | 11/1980 | Scott | 436/127 |
| 4,293,220 | 10/1981 | Denton et al. | 356/316 |
| 4,601,882 | 7/1986 | Benner | 436/127 |

FOREIGN PATENT DOCUMENTS

| | | | |
|---|---|---|---|
| 928224 | 5/1982 | U.S.S.R. | 436/173 |
| 1258403 | 12/1971 | United Kingdom . | |

OTHER PUBLICATIONS

"Consideration of as Atmospheric Pressure Microwave-Induced Helium Plasma . . . ", Slatkavitz et al., *J. of Chrom.*, 335 (1986) 117–126.
Slatkavits, et al., Journal of Chromatography, 1986, 355, 177–126.
King, et al., Anal. Chem., 1986, 58, 642–647.

*Primary Examiner*—James C. Housel
*Assistant Examiner*—Jeffrey R. Snay

[57] ABSTRACT

The oxygen-selectivity of an atomic emission detection system is enhanced by introducing a carbon-containing, preferably non-oxygenated, gas as a portion of the reagent gas. In preferred embodiments, the reagent gas is nitrogen and/or hydrogen and up to about 50 volume percent of a $C_1$–$C_4$ hydrocarbon gas.

25 Claims, 4 Drawing Sheets

METHOD AND SCAVENGER GAS FOR THE ANALYSIS OF OXYGEN-CONTAINING COMPONENTS USING ATOMIC EMISSION SPECTROMETRY

This is a continuation of application Ser. No. 064,041, filed Jun. 18, 1987 now abandoned.

BACKGROUND OF THE INVENTION

The present invention relates to the use of atomic emission spectrometry for the element-specific analysis of a sample, preferably a fractionated sample eluted from a separation means such as a gas chromatograph. More particularly, the invention relates to the use of an improved reagent (or scavenger) gas which provides increased selectivity for oxygen detection.

Atomic emission spectrometers equipped with plasma-excitation means are commonly used in many applications of chemical analysis for quantitative determination of the presence of particular elements in a multi-component sample. The spectrometers are also used in the analysis of the fractionated effluent from a separatory device such a gas chromatograph (GC). In that function, the atomic emission line for the desired element is monochromatically monitored and plotted as a function of time, correlatable with the period of time over which the various components of the fractionated sample pass through the plasma-forming stage of the spectrometer. The utility of this analytical technique, particularly in such applications as the monitoring of environmental pollutants, is critically dependent on the use of a spectrometer that is highly element-selective.

As used herein, the "selectivity" of a spectrometer or detector is the ability of the detector to reject a response from compounds not containing the specific element of interest. Selectivity is normally expressed as the ratio of the mass of a compound not containing the selected element necessary to produce the same chromatographic response as a mass of a compound that does contain that element.

The selectivity in atomic emission spectrometry is as high as 10,000 for most elements, provided the specific detector used has sufficiently high resolution and is capable of filtering spectral background "noise" (interfering signals from, for example, molecular emissions). The selectivity for oxygen, however, has been considerably lower than this with the analytical equipment and methods of the prior art. For example, in atomic emission spectrometry using atmospheric pressure microwave-induced helium plasma, oxygen normally exhibits selectivity of only about 10, which is too low to allow proper distinction between oxygenated and non-oxygenated hydrocarbons.

Improvements in the results available for atomic emission spectrometry in general have been made through the use of reagent (or scavenger) gases, which are usually injected into the stream of carrier gas (generally helium), which entrains the sample just before the inlet to the spectrometer. Reagent gases are used to prevent the deposition of soot on the lamp or discharge tube, which is a particular problem when carbon or sulfur compounds are in the sample to be analyzed. The most commonly used reagent gases have been oxygen, hydrogen, and nitrogen, the choice of the particular reagent for use being dependent upon its absence in the sample compounds of interest to avoid the production of background noise. U.S. Pat. No. 3,887,280, for example, discloses the individual use of each of these gases in the elemental analysis of a carbon-containing sample.

In the particular case of the detection of oxygen-containing compounds, for example, it has been reported that oxygen-to-carbon selectivity in spectrometers operating at atmospheric pressure with microwave-induced helium plasma can be increased by using hydrogen as the reagent gas. See Slatkavitz et al, Journal of Chromatography, 355 (1986), 117–126. More particularly, it is disclosed that the addition of about 0.1–0.4 volume percent hydrogen, based on the helium flow-rate, provides improved peak shape through reduction of anomalous "negative" responses. Nevertheless, oxygen selectivity is not reported to approach the levels generally achieved for other elements, and it is also indicated that negative responses are still obtained because of background oxygen which is often present as an impurity in the helium or which enters the system through air leaks. Accordingly, there remains a need for atomic emission spectrometry having improved selectivity for oxygen.

SUMMARY OF THE INVENTION

The present invention provides an improved method of elemental analysis of a sample which includes an oxygen-containing compound. The basic method comprises the steps of (i) introducing a mixture of the sample, an inert carrier gas therefor, and a reagent gas into an atomic emission spectrometer having plasma-excitation means; (ii) forming a plasma from said mixture, and (iii) detecting at least one oxygen or oxygen-related optical emission generated in the spectrometer. The improvement provided by the present invention comprises introducing a controlled amount of a carbon-containing gas into the mixture which enters the plasma-forming stage. In preferred embodiments, the carbon-containing gas is introduced with the basic reagent gas and replaces a portion of the reagent gas on a v/v basis. In most preferred embodiments, the reagent gas, as modified by the introduction of the carbon-containing gas, comprises nitrogen, hydrogen, or mixtures of these and up to about 20 volume percent of methane, propane, propylene, or n-butane.

The method of the present invention substantially enhances the capability to selectively detect oxygenated compounds, the importance thereof being highlighted by the fact that oxygen is the third most prevalent element (carbon and hydrogen being more abundant) in known organic compounds. A further advantage of the present invention is its applicability to existing equipment for atomic emission detection. No substantial modification of such equipment is necessary, and the invention can otherwise be practiced, and its benefits achieved, with standard spectrometers.

DETAILED DESCRIPTION OF THE INVENTION

Figure 1:
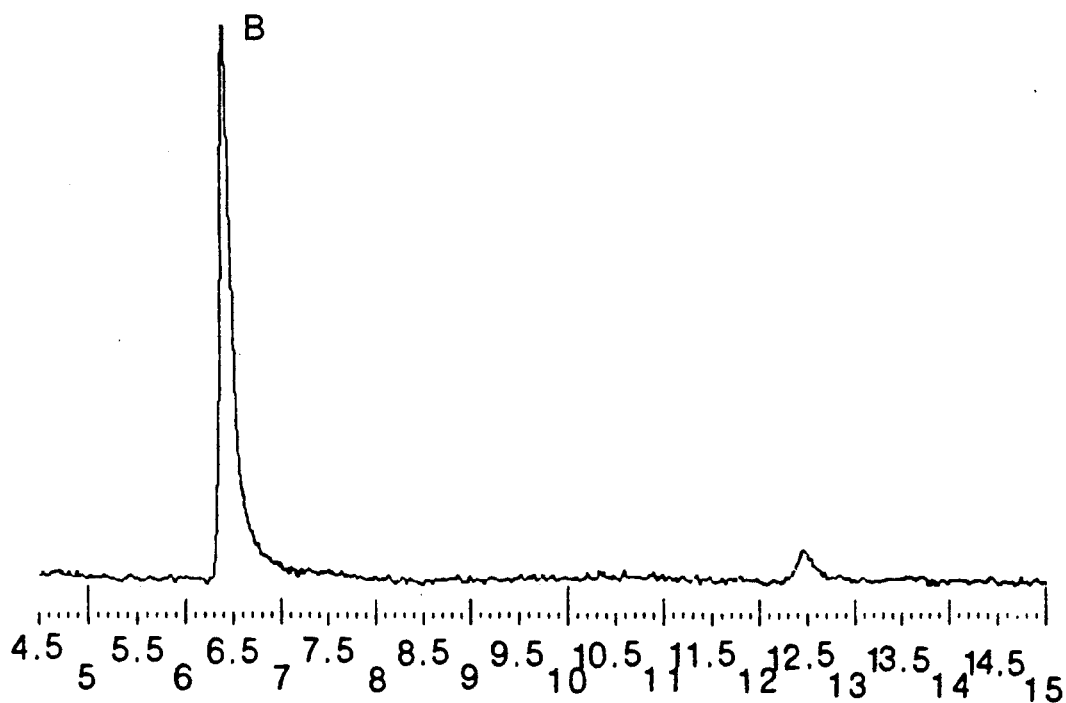
FIG. 1 is a sulphur-specific chromatogram, using oxygen as a reagent gas, of a fractionated sample of known composition.

The present invention provides an improvement in the use of atomic emission spectrometry for chemical analysis by which the oxygen selectivity of the analysis is greatly enhanced. More particularly, the invention is based on the improved oxygen selectivity obtained by the introduction of a carbon-containing gas, preferably non-oxygenated, as a portion of the reagent gas that normally accompanies the sample into the plasma-forming chamber of the spectrometer.

In the performance of atomic-emission analyses of the kind to which the present invention pertains, the sample to be analyzed and a carrier gas for that sample are directed into an atomic emission spectrometer equipped with apparatus to generate a plasma from the carrier gas and sample. The invention is particularly useful in the analysis of the fractionated effluent from a separatory device such as a gas chromatograph (GC), and the invention will hereafter be described in terms of this preferred embodiment, although it is to be understood that it is equally applicable to the analysis of an unfractionated single-component or unfractionated multi-component sample as well. With the use of such a separatory device, the effluent is directed into an atomic emission spectrometer equipped to generate a plasma from the effluent. By means of the spectrometer, the atomic emission line of the desired element within the sample is monitored and generally correlated with the passage of the various compounds contained in the fractionated sample through the plasma-forming stage of the spectrometer. Carrier gases in general use are inert gases such as helium, argon, and neon. The plasma can be generated by subjecting the gas to, for example, microwave radiation. Microwave induction of helium plasma is preferred according to the present invention.

In general practice, the hardware connection between the gas-separation device and the spectrometer is generally equipped with means for introducing a reagent gas and additional carrier gas (known as make-up gas) into the effluent of the separatory device prior to that stream's entering the spectrometer. Although these gases can be introduced into the effluent through separate ports in the effluent line, they are usually and preferably pre-combined in a common feed line and injected through a single port. The make-up gas is used primarily to maintain the effluent pressure sufficiently above atmospheric pressure to provide proper flow to the spectrometer, the plasma-forming step of which is preferably at or just above atmospheric pressure. The reagent gas and make-up gas can each be bled into the common feed line through, for example, an adjustable pressure valve or controller.

In general practice and for purposes of the present invention, flow rates of the sample plus carrier gas through a gas chromatograph vary from as little as about 0.5 ml/min (calculated at standard conditions) to as much as about 50 ml/min. The make-up gas is added to the column effluent in an amount of about 10-50 ml/min to provide a v/v ratio with the effluent in the range of about 1.0-20.0. The reagent gas is generally added in an amount sufficient to provide about 0.05-2.0 volume percent, preferably about 0.1-1.5 volume percent, of the total gas entering the plasma.

According to the present invention, the oxygen selectivity of an analytical system of the kind described above is enhanced when a controlled amount of a carbon-containing gas is introduced into the gas mixture from which the plasma is formed. Preferably the carbon-containing gas is introduced as a portion of the basic reagent gas. For the detection of oxygen-containing compounds, the reagent gas is normally nitrogen and/or hydrogen. It has been found that generally any carbon-containing gas can be used in conjunction with the basic nitrogen or hydrogen reagent gas with good results. It is preferred that the carbon-containing gas not include oxygen, although gases generated from organic compounds of low oxygen content, such as those having a carbon-to-oxygen atomic ratio of at least about 8:1, can be used. Long-chain mono-alcohols are examples of such compounds. Most preferred gases are $C_1$-$C_4$ hydrocarbon gas such as methane, ethane, ethylene, propane, propylene, n-butane, iso-butane, or butylene.

The amount of carbon-containing gas used according to the invention will vary depending upon the concentrations of any oxygenated impurities in the gases entering the plasma. Most preferably, the carbon-containing gas is introduced in an amount just below that at which carbon soot begins to deposit on the discharge tube of the atomic emission detector. This level usually must be determined empirically before each run because of the effect on soot-deposition rate of such factors as the overall gas flow rate and the possible presence of other soot-inhibiting compounds in the stream. Generally, however, it has been found that providing the carbon-containing gas in an amount of about 0.005-1.0 volume percent of the total gas entering the plasma is effective. In the preferred embodiment of the invention, the carbon-containing gas is introduced into the system as a replacement for up to about 50 volume percent, more preferably 0.1-20 volume percent, of the generally-used amount of hydrogen or nitrogen reagent gas, as described above. Most preferably, about 1.0-10.0 volume percent of the basic reagent gas is replaced by the carbon-containing gas.

In operation, the carbon-containing gas can be introduced into the mixture from which the plasma is to be generated at any point in the system. It is important only that the flow of the gas be controlled to be within the effective range. Most preferably, the carbon-containing gas and the basic nitrogen and/or hydrogen reagent gas are metered and bled into a common feed line which, in turn, is combined with the make-up gas as earlier described. Any conventional means for metering the flow of gas, such as those combining adjustable pressure controllers and flow restrictors, can be used so long as the flow of carbon-containing gas is controllable and can be maintained within the effective concentration.

The present invention is illustrated by reference to FIGS. 1-5, which depict a comparative study of the chromatograms generated by a known sample mixture both with and without the improved scavenger gas. The mixture on which the study was conducted consisted of nitro-benzene (Compound "A" in the figures), t-butyl disulfide ("B"), n-dodecane ("C"), and n-tridecane ("D") in a carrier gas of helium. Apparatus used in the study included a Hewlett Packard 5890A Gas Chromatograph with dedicated on-column injection, and a laboratory-built spectrometer having a 0.5m, f/8 concave grating mount and equipped with a solvent-dumping means as described in U.S. Pat. No. 4,517,824. Operating conditions for the GC-AED study are summarized in the following table.

| GC-AED Operating Conditions | |
|---|---|
| Chromatographic Conditions | |
| Column | 12 m cross-linked 5% phenyl methyl silicon (0.53 mm I.D.; 0.88 μm film thickness) |
| Helium flow-rate | 8 ml/min (research grade purity) |
| Injection size | 1 μl |
| Column temperature | 65° C. to 200° C. at 10° C./min (programmed) |
| Detection interface temperature | 250° C. |
| Spectroscopic Conditions | |
| Microwave plasma cavity | Modified $TM_{010}$ (with water-cooled discharge tube) at atmospheric pressure |
| Tuning device | Coaxial stubstretcher |
| Power | 120 W at 2450 MHz |
| Helium flow-rate | 50 ml/min (8 ml/min from column; 42 ml/min make-up) |
| Reagent gas flow-rate | 0.5 ml/min |
| Element detection wavelength | |
| Oxygen | 777.2 nm |
| Carbon | 193.1 nm |
| Sulfur | 180.7 nm |
| Spectral resolution | 0.075 nm |
| Entrance slit | 60.0 μm (width) by 5 mm (height) |
| Computer | Hewlett Packard Model 9836 |
| Plotter | Hewlett Packard Model 2673A |
| Photodetector | 212 pixel linear photodiode array, pixel size 60 × 600 μm |

Figure 2:
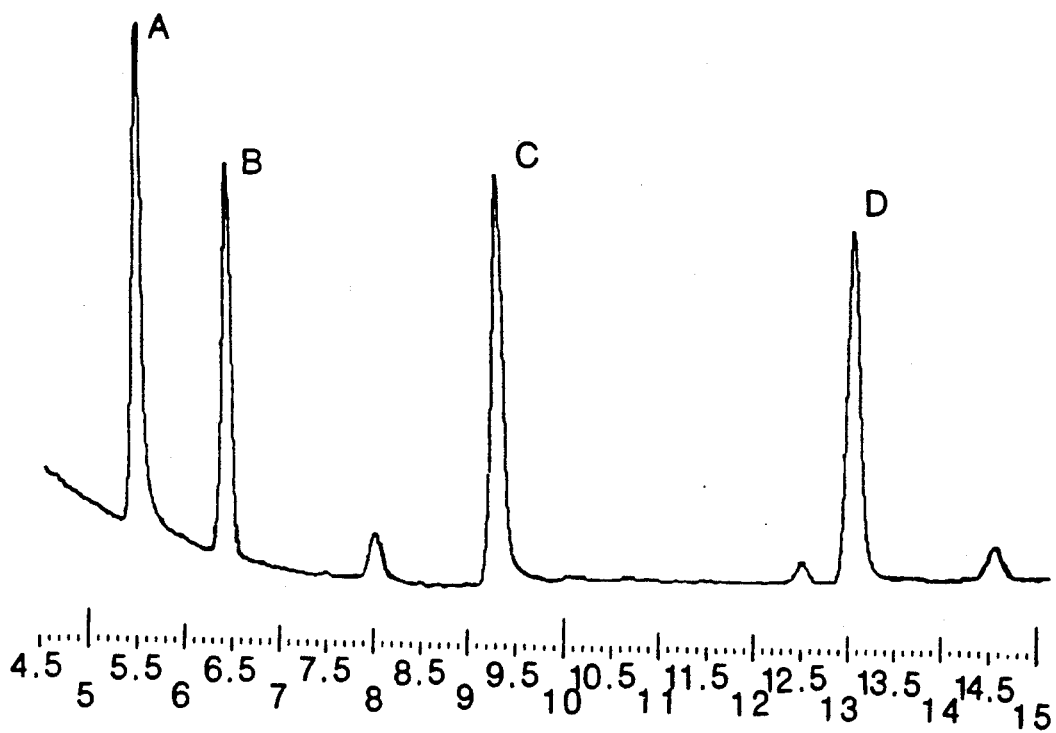
FIG. 2 is a carbon-specific chromatogram, using oxygen as a reagent gas, of the sample of FIG. 1.

FIG. 1 is a sulfur chromatogram of the sample mixture and FIG. 2 is a carbon chromatogram of the same mixture taken simultaneously at the carbon-detection wavelength. The reagent gas used in the generation of each of these control chromatograms was oxygen, about 1% by volume of total gas. As can be seen, all compounds generate sharp responses at the carbon wavelength (FIG. 2), and the selectivity for the sulfur channel alone is shown in FIG. 1 to be excellent, the only responses being to the single sulfur-containing compound (B) and a sulfur-containing impurity, which eluted at about 12.5 minutes. There is no detectable response from any of the non-sulfur containing compounds in the mixture.

Figure 4:
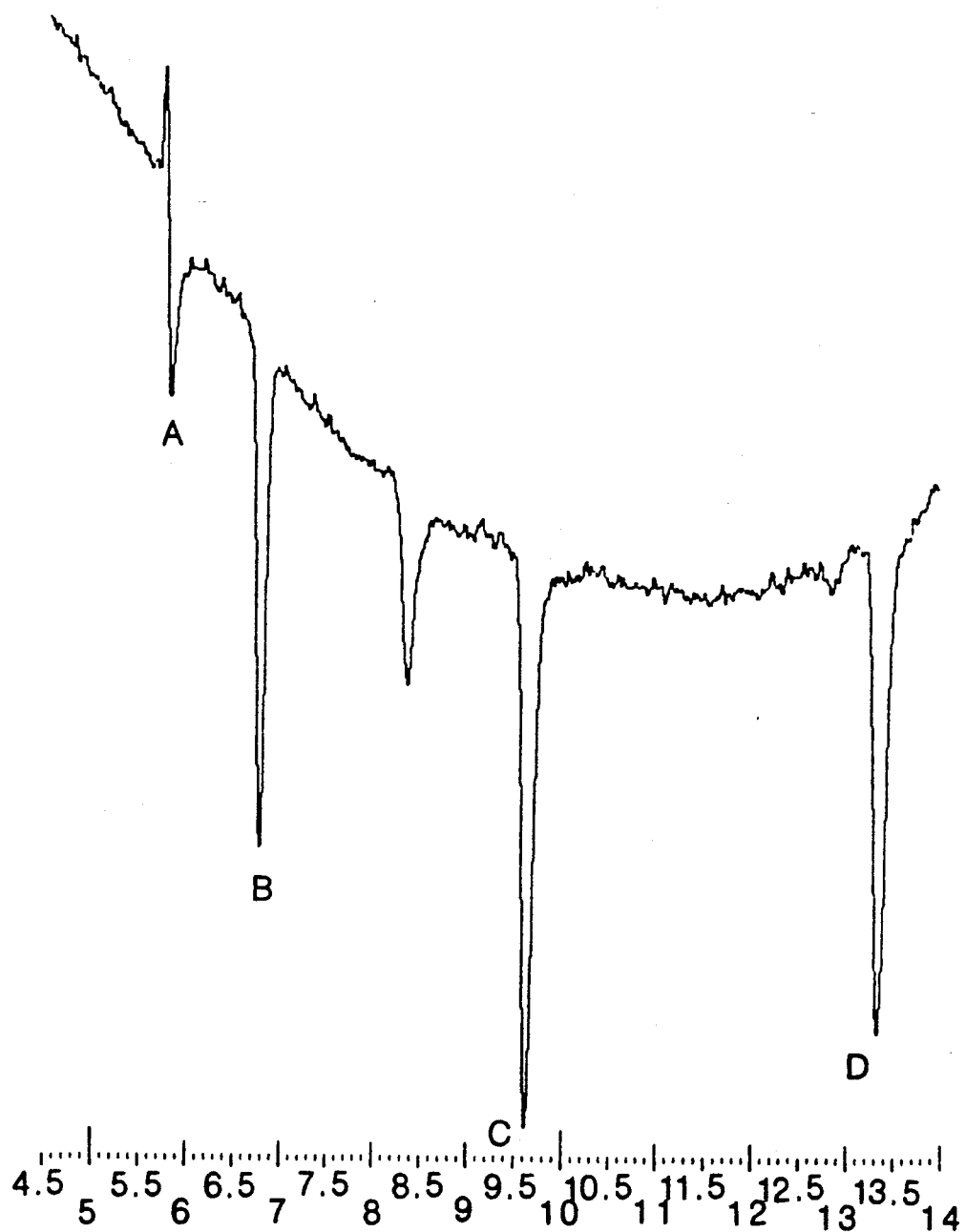
FIG. 4 is an oxygen-specific chromatogram, using hydrogen as a reagent gas, of the sample of FIG. 1.
Figure 3:
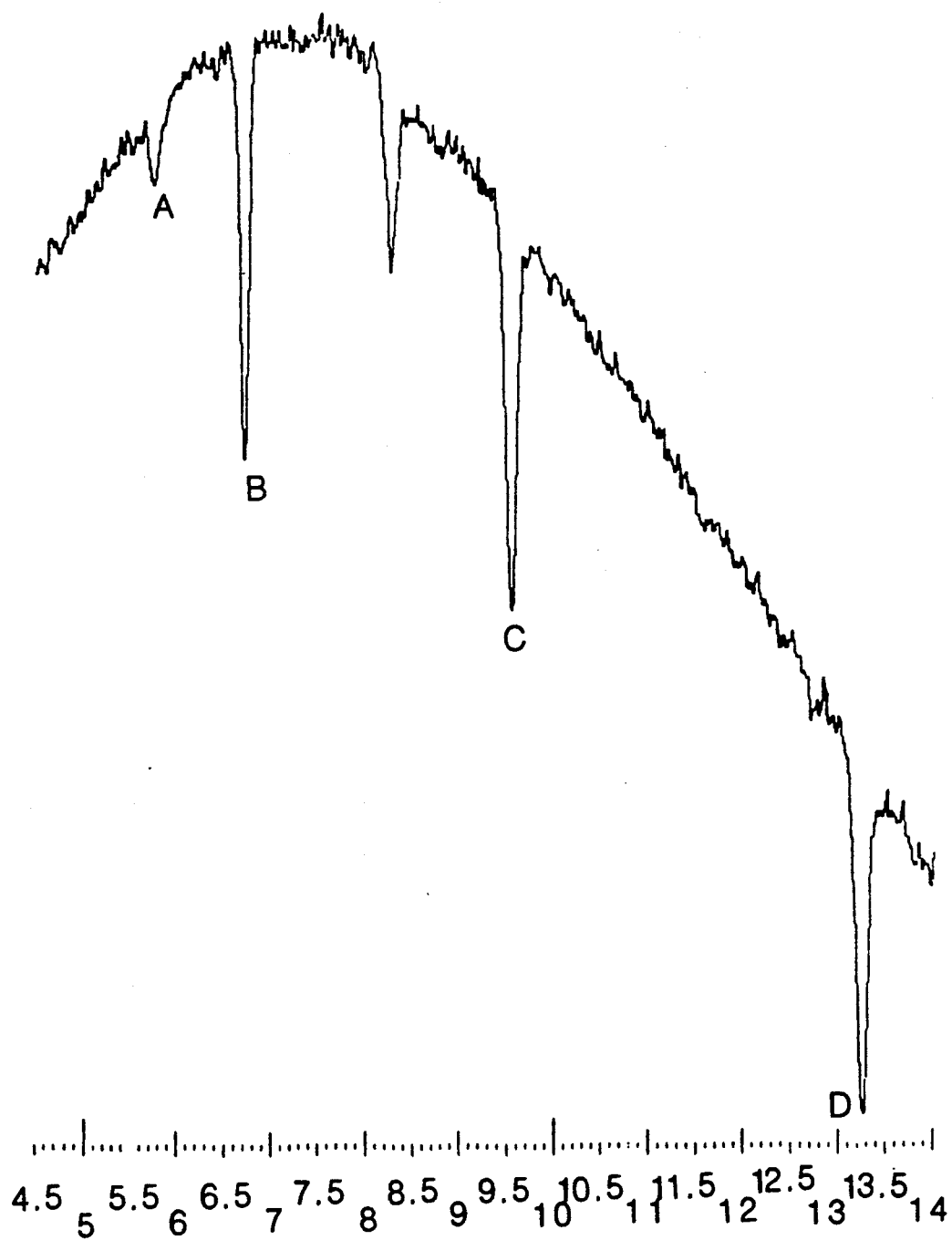
FIG. 3 is an oxygen-specific chromatogram, using nitrogen as a reagent gas, of the sample of FIG. 1.

FIGS. 3 and 4 are the oxygen chromatograms for the test mixture plotted at the oxygen wavelength using nitrogen and hydrogen, respectively, as the reagent gases at a concentration of about 1% by volume (about 0.5 ml/min) of the total helium entering the detector. These control chromatograms demonstrate the poor oxygen selectivity of existing spectrometry methods. All compounds in the mixture produce significant anomalous responses in each chromatogram (either negative peaks or zig-zag positive/negative peaks as predicted by Slatkavitz et al), demonstrating the uselessness, for practical purposes, of standard techniques for oxygen analysis.

Figure 5:
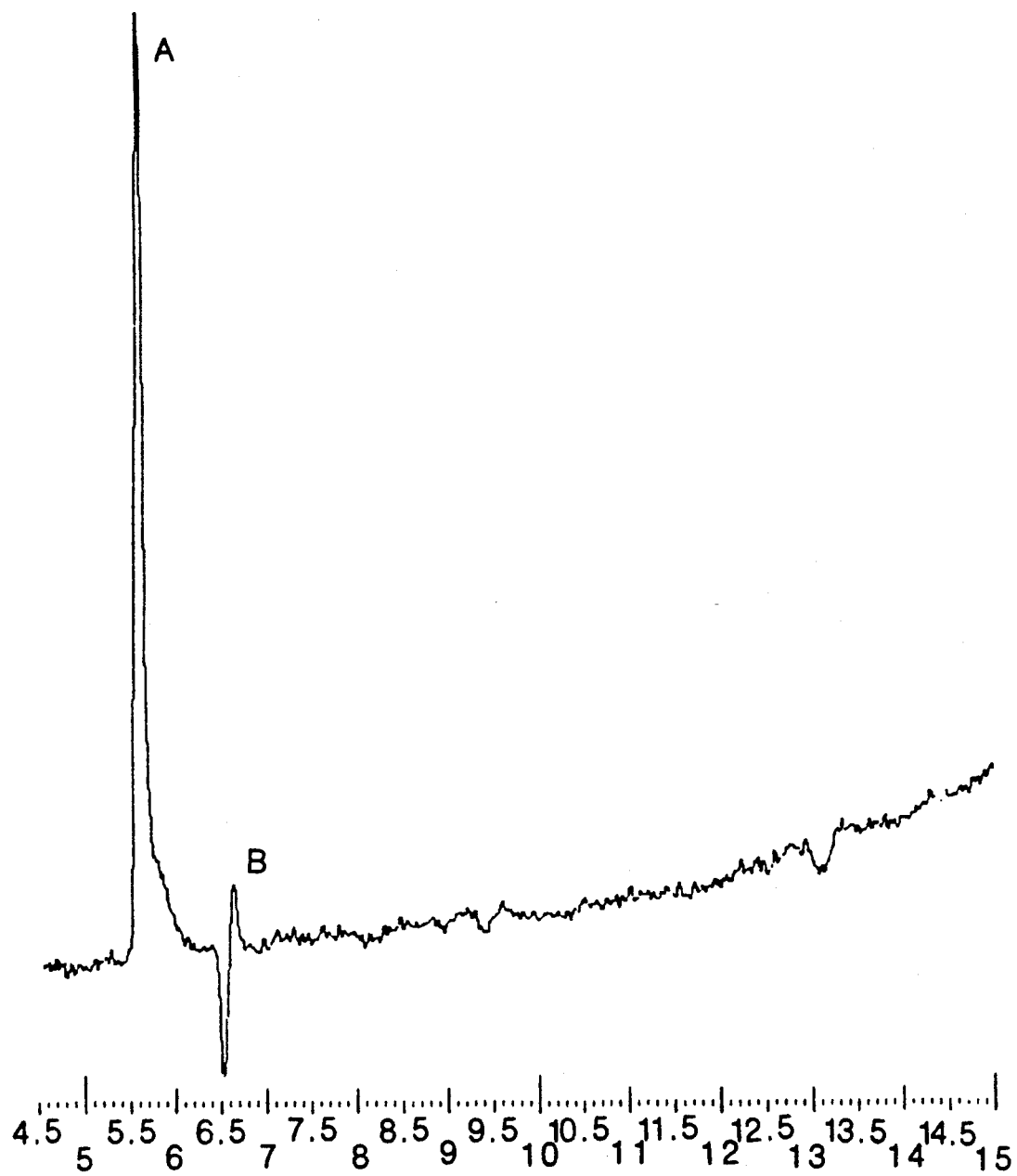
FIG. 5 is an oxygen-specific chromatogram of a sample of FIG. 1 using a 99/1 v/v mixture of hydrogen and propane as a reagent gas.

The use of the improved reagent gas of the present invention is shown in FIG. 5. The chromatogram of FIG. 5 depicts analysis of the sample mixture of FIGS. 3 and 4 using as the reagent gas a mixture of hydrogen and propane in a v/v ratio of about 99/1 (about 0.5 ml/min hydrogen mixed with about 0.005 ml/min propane), providing a total reagent gas concentration of about 1.0% by volume. The response to the single oxygenated target compound of the mixture, Compound A, is positive and strong. Comparison to either of FIGS. 3 or 4 shows that responses to the non-oxygenated target compounds are substantially reduced or eliminated.

We claim:

1. In a method of an oxygen-containing compound in a sample comprising the steps of (i) introducing a mixture of the sample, an inert carrier gas therefor, and a reagent gas into an atomic emission spectrometer having plasma-excitation means, (ii) forming a plasma from said mixture, and (iii) detecting at least one oxygen-related optical emission generated thereby, wherein the improvement comprises introducing a controlled amount of a carbon-containing gas into said mixture prior to introducing said mixture into said spectrometer.

2. The improvement of claim 1 wherein said carbon-containing gas is introduced as a portion of the reagent gas.

3. The improvement of claim 1 wherein the reagent gas comprises hydrogen and said carbon-containing gas, said carbon-containing gas being non-oxygenated and present in an amount of about 0.1–20 volume percent of said reagent gas.

4. The improvement of claim 1 wherein the reagent gas comprises hydrogen and said carbon-containing gas, said carbon-containing gas being propane or n-butane and present in an amount of about 0.1–20 volume percent of said reagent gas.

5. The improvement of claim 1 wherein the reagent gas comprises nitrogen and said carbon-containing gas, said carbon-containing gas being non-oxygenated and present in an amount of about 0.1–20 volume percent of said reagent gas.

6. The improvement of claim 1 wherein the reagent gas comprises nitrogen and said carbon-containing gas, said carbon-containing gas being propane or n-butane and present in an amount of about 0.1–20 volume percent of said reagent gas.

7. The improvement of claim 1 wherein the reagent gas comprises a mixture of hydrogen and nitrogen and said carbon-containing gas, said carbon-containing gas being present in an amount up to about 50% by volume of said reagent gas.

8. The improvement of claim 1 wherein said reagent gas comprises about equal volume parts of hydrogen and nitrogen and further comprises said carbon-containing gas, said carbon-containing gas being a $C_1$–$C_4$ hydrocarbon gas or mixture of said $C_1$–$C_4$ hydrocarbon gases, carbon-containing gas being present in an amount of about 0.1–20 volume percent of said reagent gas.

9. The improvement of claim 1 wherein said reagent gas comprises nitrogen and said carbon-containing gas, said carbon-containing gas being a $C_1$–$C_4$ hydrocarbon gas or mixture of $C_1$–$C_4$ hydrocarbon gases and present in an amount up to about 50% by volume by said reagent gas, and further wherein said carrier gas is helium and the plasma is formed by microwave induction at atmospheric pressure.

10. The improvement of claim 1 wherein said reagent gas comprises about equal volume parts of hydrogen and nitrogen and further comprises said carbon-containing gas, said carbon-containing gas being hydrocarbon gas or mixture of $C_1$–$C_4$ hydrocarbon gases and present in an amount up to about 50% by volume of said reagent gas, and further wherein said carrier gas is helium and the plasma is formed by microwave induction at atmosphere pressure.

11. The improvement of claim 1 wherein said reagent gas comprises nitrogen and said carbon-containing gas, said carbon-containing gas being present in an amount of about 1.0–10.0 volume percent of said reagent gas.

12. The improvement method of claim 11 wherein said carbon-containing gas is propane.

13. The improvement of claim 1 wherein the reagent gas comprises hydrogen and said carbon-containing gas, said carbon-containing gas being present in an amount up to about 50% by volume of said reagent gas.

14. The improvement of claim 13 wherein said carbon-containing gas is a $C_1$-$C_4$ hydrocarbon gas or mixture of said $C_1$-$C_4$ hydrocarbon gases.

15. The improvement of claim 14 wherein said sample is fractionated in a gas chromatograph before being introduced into said mixture.

16. The improvement of claim 1 wherein the reagent gas comprises hydrogen and said carbon-containing gas, said carbon-containing gas being present in an amount of about 1.0-10.0 volume percent of said reagent gas.

17. The improvement of claim 16 wherein said carbon-containing gas is propane.

18. The improvement of claim 17 wherein the sample is fractionated in a gas chromatograph before being introduced in said mixture.

19. In a method of detecting an oxygen-containing compound in a sample comprising the steps of (i) introducing a mixture of the sample, an inert carrier gas therefor, and a reagent gas into an atomic emission spectrometer having plasma-excitation means, (ii) forming a plasma from said mixture, and (iii) detecting at least one oxygen-related optical emission generated thereby, wherein the improvement comprises introducing a controlled amount of a carbon-containing gas into said mixture prior to introducing said mixture into said spectrometer, and wherein said reagent gas comprises nitrogen and said carbon-containing gas, said carbon-containing gas being present in an amount up to about 50% by volume of said reagent gas.

20. The improvement of claim 19 wherein said carbon-containing gas is a $C_1$-$C_4$ hydrocarbon gas or mixture of said $C_1$-$C_4$ hydrocarbon gases.

21. The improvement of claim 19 wherein the sample is fractionated in a gas chromatograph before being introduced in said mixture.

22. The improvement of claim 19 wherein said carbon-containing gas is propane, said propane being present in an amount of about 1.0-10.0 volume percent of said reagent gas, and further wherein the sample is fractionated in a gas chromatograph before being introduced in said mixture.

23. In a method of detecting an oxygen-containing compound in a sample and which sample has been fractionated in a gas chromatograph, which method comprises the steps of (i) introducing a mixture of said sample, an inert carrier gas therefor and a reagent gas selected from the group consisting of hydrogen, nitrogen or mixtures thereof into an atomic emission spectrometer having plasma-excitation means and a discharge tube, (ii) forming a plasma from said mixture by microwave induction, and (iii) detecting at least one oxygen-related optical emission generated thereby, wherein the improvement comprises introducing a gas selected from the group consisting of $C_1$-$C_4$ hydrocarbon gas or mixtures thereof into said mixture after fractionation of said sample in an amount below that at which soot begins to deposit on the discharge tube of said atomic emission detector.

24. In a method of detecting an oxygen-containing compound in a sample comprising the steps of (i) introducing a mixture of the sample, an inert carrier gas therefor, and a reagent gas into an atomic emission spectrometer having plasma-excitation means, (ii) forming a plasma from said mixture, and (iii) detecting at least one oxygen-related optical emission generated thereby, wherein the improvement comprises introducing a controlled amount of a carbon-containing gas to said mixture prior to introducing said mixture into said spectrometer, and said reagent gas comprises hydrogen and said carbon-containing gas, said carbon-containing gas being present in an amount up to about 50% by volume of said reagent gas, and said sample being fractionated in a gas chromatograph before being introduced in said mixture.

25. In a method of detecting an oxygen-containing compound in a sample comprising the steps of (i) introducing a mixture of the sample, an inert carrier gas therefor, and a reagent gas into an atomic emission spectrometer having plasma-excitation means, (ii) forming a plasma from said mixture, and (iii) detecting at least one oxygen-related optical emission generated thereby, wherein the improvement comprises introducing a controlled amount of a carbon-containing gas into said mixture prior to introducing said mixture into said spectrometer, wherein said reagent gas comprises about equal volumes of hydrogen and nitrogen and further comprising said carbon-containing gas, said carbon-containing gas being a $C_1$-$C_4$ hydrocarbon gas or mixture thereof in an amount of about 0.1-20 volume percent of said reagent gas, and wherein said sample is fractionated in a gas chromatograph before being introduced in said mixture.

* * * * *